United States Patent [19]

Drtina et al.

[11] Patent Number: 5,124,454
[45] Date of Patent: Jun. 23, 1992

[54] POLYCYCLIC DIAMINES AND METHOD OF PREPARATION

[75] Inventors: Gary J. Drtina, Woodbury; Leif Christensen, St. Paul, both of Minn.

[73] Assignee: Minnesota Mining and Manufacturing Company, St. Paul, Minn.

[21] Appl. No.: 620,258

[22] Filed: Nov. 30, 1990

[51] Int. Cl.$^5$ .......................................... C07D 221/22
[52] U.S. Cl. ...................................... 546/43; 546/14; 546/22
[58] Field of Search .............................. 546/43, 14, 22

[56] References Cited

U.S. PATENT DOCUMENTS

| 1,947,732 | 2/1934 | Parkes | 204/74 |
| 4,194,046 | 3/1989 | Junghans | 546/259 |
| 4,929,622 | 5/1990 | Allen et al. | 546/43 |

FOREIGN PATENT DOCUMENTS

247900A1 10/1983 Fed. Rep. of Germany .

OTHER PUBLICATIONS

Synthesis of Pyridines by Electrochemical Methods: by J. E. Toomey, Jr. in Advances in Heterocyclic Chemistry, vol. 37, 1984, pp. 167–215.
Nonaka, et al., Electrochemical Acta, 1977, 22, pp. 271–277.
Ferles, et al., Collect. Czech. Chem. Commun., 1975, p. 2183.

*Primary Examiner*—Mukund J. Shah
*Assistant Examiner*—Y. N. Gupta
*Attorney, Agent, or Firm*—Gary L. Griswold; Walter N. Kirn; Carolyn V. Peters

[57] ABSTRACT

Polycyclic diamines, incorporating a basic framework similar to [3.3.3]propellane, and derivatives of the basic polycyclic diamines and a process for preparing same are provided. The diamines are prepared by subjecting bispyridine compounds to electroreductive coupling in an acidic solution. The polycyclic diamines and derivatives thereof are useful as chain extenders, crosslinking agents and curatives in various polymer systems.

12 Claims, No Drawings

POLYCYCLIC DIAMINES AND METHOD OF PREPARATION

This invention relates to polycyclic diamines, derivatives thereof, and processes for preparing same. The polycyclic diamines and the derivatives thereof are useful as chain extenders, crosslinking agents, and curatives in various polymer systems.

Electroreduction of pyridines is well known. U.S. Pat. No. 1,947,732 (Parkes) discloses electrochemical reduction of pyridine to piperidine at a lead cathode in aqueous sulfuric acid. Such electroreductions are often accompanied with the formation of bipyridyls and/or bypiperidyls in minor amounts as reported in "Synthesis of Pyridines by Electrochemical Methods" by J. E. Toomey, Jr. in *Advances in Heterocyclic Chemistry*, Vol. 37, 1984, pp 167-215.

U.S. Pat. No. 4,194,046 (Junghans) discloses an electroreductive coupling process in liquid ammonia wherein pyridine dimerization is preferred and results in the production of 4,4'-dipyridyls from 4-unsubstituted pyridines.

Pyridines have also been utilized as starting materials in intermolecular crossed hydrocoupling reactions as reported in Nonaka, T., Sekine, T., Odo, K., Sugino, K., *Electrochemical Acta*, 1977, 22, pp 271-77.

The above examples of electroreductive coupling or dimerization of pyridines describe generation of an individual carbon-carbon bond through intermolecular bond formation. The formation of more than one carbon-carbon single bond during single stage electroreduction of pyridines, leading to a polycyclic structure, is not widely observed. An example is reported in Ferles, M., Lebl, M., Stern, P., Trska, P., *Collect. Czech. Chem. Commun.*, 1975, pp 2183-191, wherein the preparation of tricyclic piperidyl derivatives from the electroreduction of substituted pyridines is disclosed. The product of the reaction was a complex mixture, and the components of the mixture were not completely characterized.

German Patent DD 247900 A1 describes the formation of a tricyclic piperidyl derivative, via a twostage electrosynthetic route, starting with a pyridinium salt and proceeding through a dihydropyridine dimer intermediate.

Briefly, in one aspect, the present invention provides polycyclic diamines and derivatives thereof. The polycyclic diamines of this invention incorporate a basic framework similar to [3.3.3]propellanes and bear diamine functionality and hereinafter will be referred to as "pipropels." The polycyclic diamines and derivatives thereof are represented by Formula I

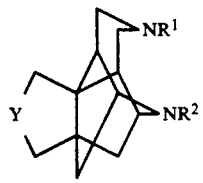

Y is —CH$_2$—, —NR$^3$—, —S—, or —O—.

R$^1$, R$^2$, and R$^3$ are independently selected from hydrogen, alkenyl or alkenylene containing 2 to 20 carbon atoms; alkyl or alkylene containing 1 to 20 carbon atoms; aryl or arylene containing 5 to 12 ring atoms in which up to 5 ring atoms may be selected from S, Si, N, O, and P heteroatoms; cycloalkyl or cycloalkylene containing 3 to 12 ring atoms in which one or more ring atoms may be selected from S, Si, N, O, and P heteroatoms; and acyl, wherein acyl is defined as

wherein R$^4$ is described as for R$^1$ to R$^3$. The aforementioned moieties can further include one or more of the following functional groups: aryl, amide, thioamide, ester, thioester, ketone (including oxocarbons), thioketone, nitrile, nitro, sulfide, sulfoxide, sulfone, disulfide, tertiary amine, ether, urethane, dithiocarbamate, quarternary ammonium and phosphonium, halogen, silyl, siloxy, and the like, wherein the functional groups requiring substituents are substituted with hydrogen.

In another aspect of the present invention, additional derivatives of pipropel are provided, and represented by Formula II

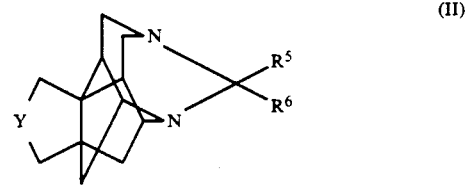

wherein Y is as described above; R$^5$ and R$^6$ are described as R$^1$ and R$^2$ and further, R$^5$ and R$^6$ taken together with the carbon atom to which they are joined, form a carbocyclic ring of 3 to 12 ring atoms, in addition to carbon, the ring atoms may be selected from S, Si, N, O, and P heteroatoms.

In a further aspect of the present invention, animal derivatives of pipropel are represented by Formula III:

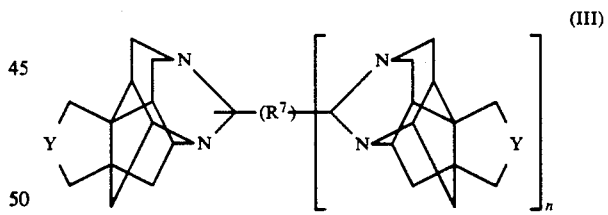

wherein Y is as described above; R$^7$ is selected from a group consisting of an arylene, an alkylene, a cycloalkylene, and an alkenylene, all as described above and further, R$^7$ taken together with the animal carbons to which it is joined, form a carbocyclic ring of 3 to 12 ring atoms, in addition, the ring atoms may be selected from S, Si, N, O and P heteroatoms; n is an integer 1, 2, or 3.

In another aspect, the present invention provides a process for preparing the polycyclic diamines of the invention comprising mixing a bispyridine compound with an electrolyte and subjecting said mixture to electroreductive coupling.

The pipropel compounds, shown in Formula I, are prepared by a single stage electroreductive coupling reaction, as described below, of the bispyridine compounds and represented by Formula IV:

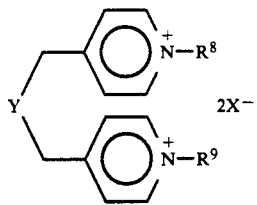

(IV)

wherein Y is —CH$_2$—, —NR$^{3'}$—, —S—, or —O—; each R$^{3'}$, R$^8$ and R$^9$ are independently selected from hydrogen or lower alkyl, having 1 to 4 carbon atoms, and X is a counterion selected from, but not limited to chloride, bromide, iodide, sulfate, bisulfate, fluoroborate, perchlorate, and trifluoroacetate.

The polycyclic diamines and derivatives thereof of this invention are useful as curing agents for resins, such as epoxies or phenolics and as chain extenders for polymers, such as polyurethanes or polyureas.

In this application:

"aminal" means a nitrogen analog of an acetal;

"electrolyte" means a solution that has sufficient acid strength to render a basic starting material essentially protonated.

One class of pipropel derivatives of the invention is prepared by further substitutions on the depicted nitrogen atoms. Typical arylation, acylation or alkylation reactions, as described in March, *Advanced Organic Chemistry*, 3rd ed., John Wiley & Sons (1985), can be carried out using well-known methods to form derivatives of the polycyclic diamines, represented by Formula I.

The animal derivatives represented by Formula II or III are produced by reacting pipropel with aldehydes, ketones, alkyl dihalides, and alkyne Michael acceptors that are capable of undergoing two nucleophilic additions at the same carbon atom.

Examples of derivatives according to Formula II or III include, but are not limited to:

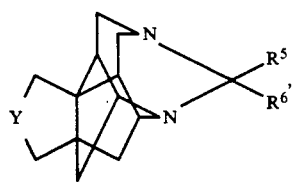

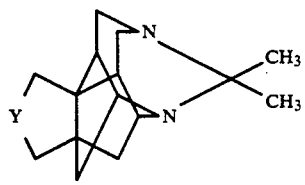

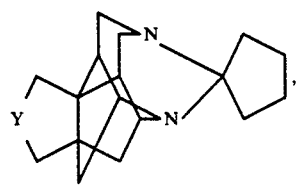

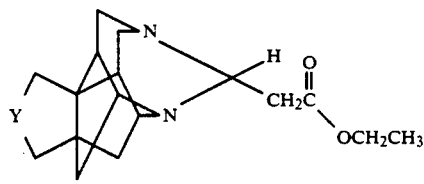

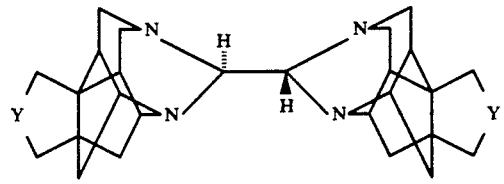

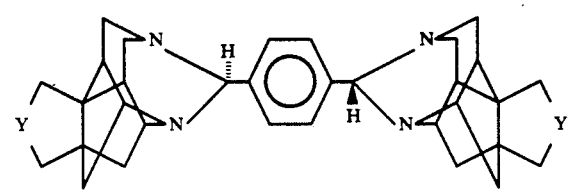

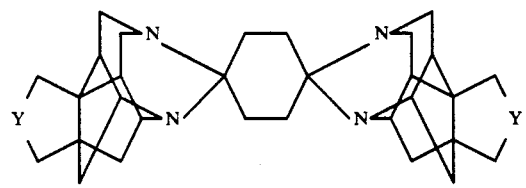

The electroreductive coupling reaction used to prepare the pipropel compounds of the invention can be performed in a divided or an undivided cell such as a standard glass H-cell, as described in *Organic Electrochemistry* (2nd Ed.), M. Baizer and H. Lund, eds., Marcel Dekker, New York, 1983, Chap. 5, p 168. For large scale runs, the reaction can be carried out in a plate and frame flow cell as described in *Technique of Electroorganic Synthesis, Part III*, N. Weinberg and B.Tilak, ed., John Wiley & Sons, New York, 1982, Chap. III, p 179.

Cathode materials useful for the preparation of the compounds of the invention include, but are not limited to, high hydrogen overvoltage materials such as mercury, lead or cadmium. Since the coupling reaction takes place at the cathode, any anode material stable under electrolysis conditions may be used.

The electroreductive coupling can occur in aqueous, or aqueous organic electrolytes, comprising solutions of Bronsted acids, such as sulfuric, fluoroboric, and trifluoroacetic acids. Although the preferred electrolyte is aqueous sulfuric acid, any electrolyte may be selected that has sufficient acid strength to render a basic starting material essentially protonated.

Although the preferred method of electrolysis to obtain the compounds of this invention takes place under constant current conditions, the reductive coupling could also be performed using controlled potential electrolysis, as understood by those skilled in the art. Typical current densities are between 1 and 5000 milliamps(mA)/cm$^2$, preferably between 10 and 1000 mA/cm$^2$.

The reaction is preferably carried out at a temperature in the range of about 0° C. to 50° C., more preferably about 10° C. to 40° C., most preferably at room temperature.

The aspects and advantages of this invention are further illustrated by the following examples. The specific details are set forth to provide a more thorough understanding of the present invention. However, the particular materials and amounts thereof recited in these examples, as well as details of other conditions, should not be construed to unduly limit this invention. In other instances, well known processes and reactants have not been described in detail in order not to unnecessarily obscure the present invention. All starting materials are commercially available for example from Aldrich Chemical Company, unless otherwise stated.

EXAMPLE 1

A plate and frame electrochemical cell (MP cell, available from ElectroCell AB, Sweden), equipped with two lead electrodes (100 cm² area) and a cation exchange membrane (Nafion™ 324 available from Dupont Company, Wilmington, Del.), was assembled. A mixture of 4,4'-trimethylenedipyridine (25 grams) and 0.95 M sulfuric acid (400 mL) was added to the cathode reservoir. Aqueous 5% sulfuric acid (400 mL) was added to the anode reservoir. After a constant flow rate of 2L/min. through both compartments was achieved, a constant current of 12 amperes ("A" or "amps") was maintained. Electrolysis was terminated after passage of 166,000 coulombs. The catholyte was recovered and adjusted to pH 10–13 by adding 6N sodium hydroxide (NaOH) solution. The aqueous solution was extracted with chloroform. The organic solution was then washed with saturated aqueous sodium chloride (NaCl) and dried over magnesium sulfate (MgSO₄). Concentration in vacuo produced a yellow oil that solidified on standing. Recrystallization of the yellow crystals from acetonitrile produced white crystals (mp 166°–168° C.) of pure pipropel, having the structure:

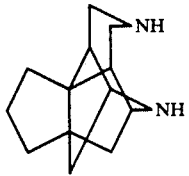

The structure was confirmed by ¹H NMR, ¹³C NMR, and mass spectroscopy.

EXAMPLE 2

A standard glass H-cell (200 mL volume, glass frit separator) was equipped with a mercury pool cathode 12 cm² area), a magnetic stirrer, and a platinum foil anode. The cell reservoir was filled with 2 M sulfuric acid (130 mL) and placed in a water bath maintained at room temperature. The catholyte was purged with nitrogen. Bis(4-pyridylmethyl) amine hydrochloride (4.0 grams) was added to the catholyte and constant current electrolysis was initiated at 0.8 A. The reaction progress was followed by gas chromatography and after passage of 11,060 coulombs, all the substrate had been consumed and the electrolysis was terminated. The catholyte was recovered and adjusted to pH 11–12 with 50% NaOH. The pH-adjusted catholyte was extracted with chloroform (2×70 mL). The extract was dried over MgSO₄. Evaporation of the organic phase left a colorless oil that partially solidified on standing.

The semi-solid product was triturated with a few milliliters of acetonitrile to produce a white precipitate. The white precipitate was filtered and rinsed with additional cold acetonitrile to produce azapipropel as a white solid with (mp 188°–190° C.), having the structure

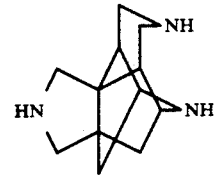

The structure was confirmed by ¹H NMR, ¹³C NMR, and mass spectroscopy.

EXAMPLE 3

A mixture of 4-(hydroxymethyl)pyridine (2.0 grams), tetrabutylammonium bisulfate (0.3 gram), and aqueous 50% NaOH solution was stirred at room temperature as solid 4-(chloromethyl)pyridine hydrochloride (3.0 grams) was added slowly. After 48 hours, the mixture was diluted with water and extracted with chloroform. The combined organic layers were washed with saturated aqueous NaCl solution and dried over MgSO₄. Concentration in vacuo produced an oil that was identified as bis(4-picolyl) ether by gas chromatography-mass spectroscopy (GC-MS). The product was used as the starting material without further purification.

A plate and frame electrochemical cell (Micro Cell, Electro Cell AB, Sweden) was assembled as described in Example 1. A solution of bis(4-picolyl)ether (2.0 grams) in 1M sulfuric acid (40 mL) was added to the cathode reservoir. 1M sulfuric acid (40 mL) was added to the anode reservoir. Electrolysis was initiated at a constant current of 1.0 A. After passage of 50,200 coulombs, analysis by gas chromatography indicated that the starting material had been consumed. Electrolysis was then terminated. The catholyte was adjusted to pH 9–10 by addition of 6N NaOH solution. The aqueous solution was then extracted with chloroform. The resulting organic solution was washed with saturated aqueous NaCl and then dried over MgSO₄. Concentration in vacuo produced a yellow oil. Recrystallization of the yellow oil from chloroform produced white crystals (mp 230° C. decomposition) of pure oxapipropel, having the structure

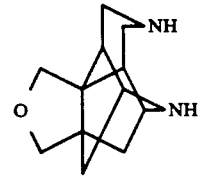

The structure was confirmed by ¹H NMR, ¹³C NMR, and mass spectroscopy.

EXAMPLE 4

Pipropel (2.0 grams, as prepared in Example 1), was added to a solution of powdered potassium hydroxide (1.7 grams) in ethanol (20 mL). The resulting mixture was treated with 2-iodopropane (10.5 grams) and then heated at reflux. After 26 hours, the mixture was allowed to cool and diluted with water (100 mL). The diluted mixture was extracted with chloroform (3×50 mL). The organic solution was dried over MgSO₄ and then concentrated in vacuo. Recrystallization of the residue from acetone/ether produced yellow crystals (mp 157° C.) of N,N'-diisopropylpipropel, having the structure

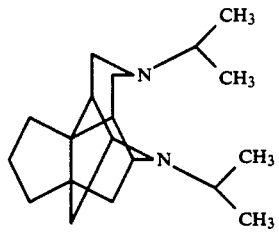

The structure was confirmed by ¹H NMR, ¹³C NMR, and mass spectroscopy.

EXAMPLE 5

A solution of 4,4'-trimethylenedipyridine (20 grams) in chloroform (10 mL) was treated with 2-iodopropane (68 grams). The mixture was heated at reflux. After refluxing for 24 hours, the biphasic mixture was allowed to cool to room temperature. The dark colored lower phase was separated and concentrated in vacuo. The concentrate solidified upon standing. Recrystallization from acetone produced a tan solid of N,N'-diisopropyl-4,4'-trimethylene dipyridinium iodide. The compound was characterized by H NMR and utilized as starting material without additional purification A glass H-cell, as described in Example 2, was filled with 2M aqueous sulfuric acid (150 mL) and maintained at room temperature. After the catholyte was purged with nitrogen, the starting material (5.0 grams) was added to the catholyte and electrolysis was initiated at a constant current of 0.93 A. After passage of 12,450 coulombs, the electrolysis was discontinued. The catholyte was recovered and adjusted to pH 10–13 with 6N NaOH solution. The adjusted catholyte was extracted with chloroform (2×75 mL). The combined organic solution was dried over MgSO₄ and evaporated in vacuo to produce a colorless oil. The colorless oil was identified as N,N'-diisopropylpipropel by capillary gas chromatography coinjection with the product from Example 4. The structure is shown in Example 4.

EXAMPLE 6

A mixture of pipropel (25.3 grams, as prepared in Example 1), and acetone (400 mL) was stirred at room temperature under argon. After 12 hours, the reaction mixture was concentrated in vacuo. Recrystallization of the residue from hexane produced pipropel isopropylidene animal, a white solid (mp 59°–61° C.), having the structure

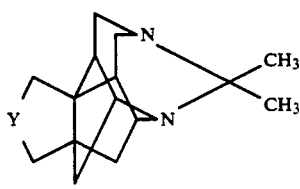

The structure was confirmed by ¹H NMR, ¹³C NMR, and mass spectroscopy.

EXAMPLE 7

A mixture of pipropel (12.0 grams, as prepared in Example 1), and glyoxal (4.8 grams) in water (90 mL) was stirred overnight at room temperature. The thick, cream colored slurry was filtered to yield an animal as a mixture of isomers. Recrystallization from methanol produced a white solid identified by ¹H NMR as a 7:1 mixture of animal isomers, having the structures

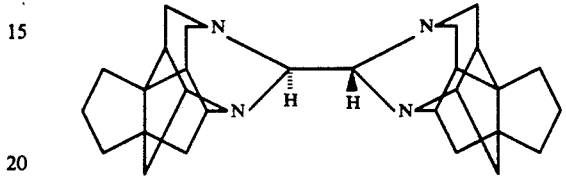

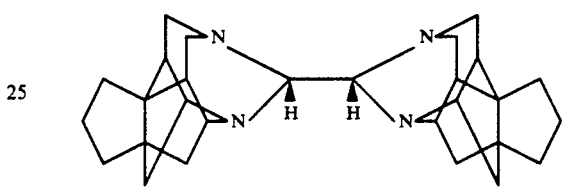

EXAMPLE 8

A mixture of pipropel (1.02 grams, as prepared in Example 1), and ethanol (25 mL) was stirred and heated at reflux as ethyl propiolate (0.50 gram) was added dropwise. After 4 hours at reflux, the mixture was concentrated in vacuo to produced a yellow solid which was identified as an animal, having the structure

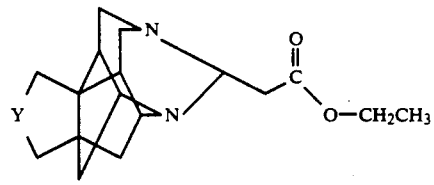

The structure was confirmed by ¹H NMR, ¹³C NMR, and mass spectroscopy.

EXAMPLE 9

Pipropel (10.2 grams, as prepared in Example 1), triethyl amine (20 mL) and chloroform (30 mL) were added to a 250 mL 3-necked flask equipped with mechanical stirrer, reflux condenser and addition funnel. The resulting mixture was cooled to 0° C. A solution of acetyl chloride (11.8 grams) in chloroform (20 mL) was then added at a rate to cause a gentle reflux. After the addition, the reaction mixture was stirred at room temperature for 2 hours. The reaction mixture was poured into 1M hydrochloric acid (200 mL). The organic layer was separated, washed with saturated aqueous NaCl, dried over MgSO₄ and evaporated to produce a yellow oil. Addition of acetone (10 mL) led to the formation of a precipitate upon standing. After filtering, yellow crystals (10.6 grams) were isolated and recrystallized from acetone to produce cream colored crystals of N,N'- diacetylpipropel (mp 173°–175° C.), having the structure

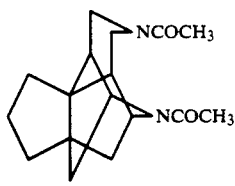

The structure was confirmed by $^1$H NMR, $^{13}$C NMR, and mass spectroscopy.

EXAMPLE 10

A mixture of pipropel (10.0 grams, as prepared in Example 1), cyclopentanone (4.4 grams), and toluene (50 mL) was stirred at room temperature for 16 hours. The resulting mixture was heated at reflux under Dean-Stark conditions. After 2 hours, the mixture was allowed to cool and then concentrated in vacuo. The residue was recrystallized from hexane to produce cream-colored crystals (mp 245°–250° C. decomposition), having the structure

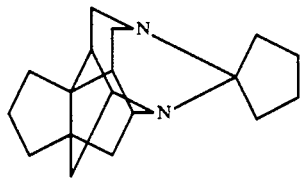

The structure was confirmed by $^1$H NMR, $^{13}$C NMR, and mass spectroscopy.

EXAMPLE 11

A biphasic mixture of pipropel (1.0 grams, as prepared in Example 1), dichloromethane (25 mL), and 2N aqueous NaOH (11 mL) was stirred vigorously at room temperature for 16 hours. The organic phase was separated and then washed with saturated aqueous NaCl. After the organic solution had been dried over MgSO$_4$, it was concentrated in vacuo to produce an animal, having the structure

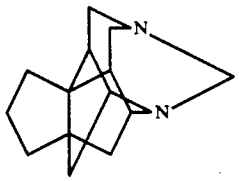

The structure was confirmed by $^1$H NMR, $^{13}$C NMR, and mass spectroscopy.

EXAMPLE 12

A solution of pipropel (10.0 grams, as prepared in Example 1), in toluene (50 mL) was treated with 1,4-cyclohexanedione (2.9 grams). The resulting mixture was heated at reflux under Dean-Stark conditions for 4 hours, during which time period a precipitate was formed. After the mixture had cooled to room temperature, it was filtered to produce a tan solid that was identified as the aminals, having the structures

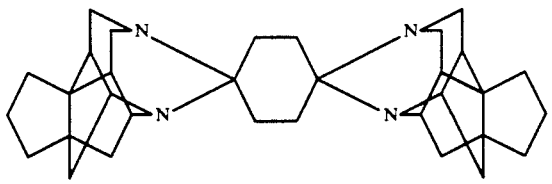

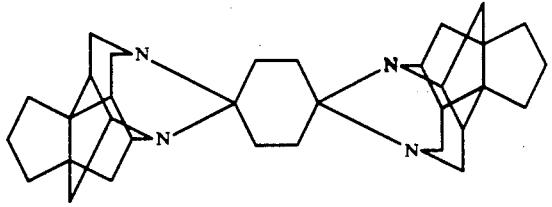

Structures were identified by high resolution mass spectroscopy.

EXAMPLE 13

Terephthalaldehyde (0.33 gram) was added to a stirred suspension of pipropel (1.00 gram, as prepared in Example 1), in toluene (8.0 mL). The resulting mixture was stirred at room temperature. After 24 hours, the mixture had become a thick slurry. After dilution with toluene, the mixture was filtered to provide the aminals, having the structures

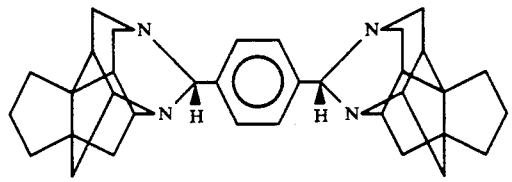

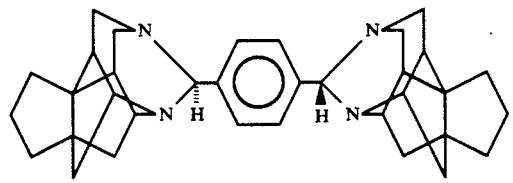

The structures were identified by high resolution mass spectroscopy.

EXAMPLE 14

A solution of isophorone diisocyanate (2.0 grams) in toluene (20 mL) was added rapidly to a solution of Jeffamine TM DU-700 (available from Texaco Chemical Company) in toluene (10 mL). While the resulting mixture was stirred at room temperature, a solution of pipropel (1.38 grams, as prepared in Example 1), in isopropyl alcohol/toluene (1:5) (30 mL) was added dropwise. After 18 hours at room temperature the reaction mixture was cast into a tough transparent film.

EXAMPLE 15

Pipropel (1.4 grams, as prepared in Example 1), in chloroform (0.3 mL) was mixed with EPON TM Resin 828 (2.5 grams) (available from Shell Chemical Company) and kept at ambient conditions. After several minutes a strong exotherm was exhibited and residual solvent was evaporated. After 2 hours, the reaction mixture had cured to a light yellow glass.

What is claimed:

1. Polycyclic diamines and derivatives thereof represented by Formula I

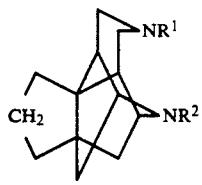
(I)

wherein $R^1$, $R^2$, and $R^3$ are independently selected from hydrogen, alkenyl or alkenylene containing 2 to 20 carbon atoms, alkyl or alkylene containing 1 to 20 carbon atoms, aryl or arylene containing 5 to 12 ring atoms in which up to 5 ring atoms may be selected from S, Si, N, O, and P heteroatoms, cycloalkyl or cycloalkylene containing 3 to 12 ring atoms in which one or more ring atoms may be selected from S, Si, N, O, and P heteroatoms, and acyl, wherein acyl is

wherein $R^4$ is described as for $R^1$ to $R^3$, and further $R^1$, $R^2$, $R^3$, and $R^4$ may include functional groups selected from the group consisting of aryl, amide, thioamide, ester, thioester, ketone (including oxo-carbons), thioketone, nitrile, nitro, sulfide, sulfoxide, sulfone, disulfide, tertiary amine, ether, urethane, dithiocarbamate, quarternary ammonium and phosphonium, halogen, silyl, and siloxy, wherein the functional groups requiring substituents are substituted with hydrogen.

2. A derivative according to claim 1, identified as N,N'-diisopropylpipropel and represented by

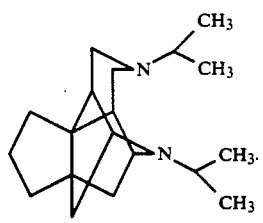

3. A derivative according to claim 1, identified as N,N'-diacetylpipropel and represented by

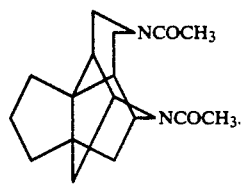

4. Derivatives of the polycyclic diamines of claim 1 comprising compounds represented by Formula II:

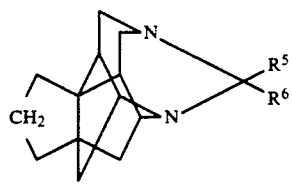
(II)

—$CH_2$—, $R^5$ and $R^6$ are described as $R^1$ and $R^2$ in claim 1 and further, $R^5$ and $R^6$ taken together with the carbon atom to which they are joined, form a carbocyclic ring of 3 to 12 ring atoms, in addition to carbon, the ring atoms may be selected from S, Si, N, O, and P heteroatoms.

5. A derivative according to claim 4, identified as pipropel isopropylidene and represented by

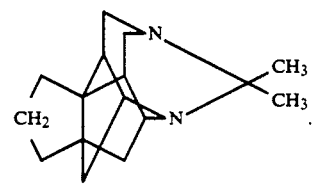

6. A derivative according to claim 4, represented by

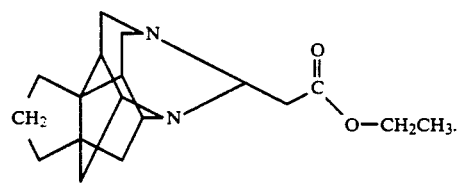

7. A derivative according to claim 4, represented by

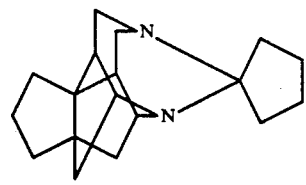

8. A derivative according to claim 4, represented by

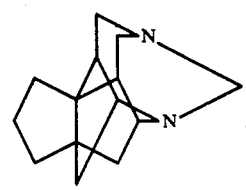

9. Derivatives of the polycyclic diamines of claim 1 comprising compounds represented by Formula III:

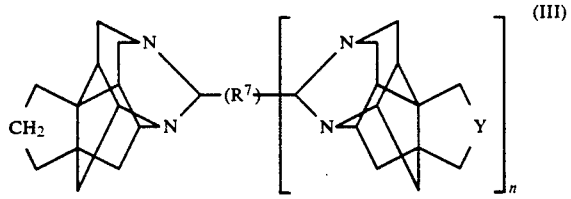

wherein —CH₂—, $R^7$ is selected from a group consisting of a arylene, an alkylene, a cycloalkylene, and alkenylene, and further $R^7$ taken with the animal carbons, to which it is joined form a carbocyclic ring of 3 to 12 ring atoms, in addition, the ring atoms may be selected from S, Si, N, O and P heteroatoms; and n is an integer 1, 2, or 3.

10. Derivatives according to claim 9, represented by

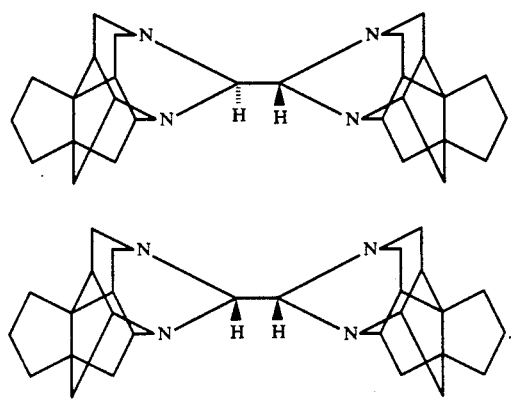

11. Derivatives according to claim 9, represented by

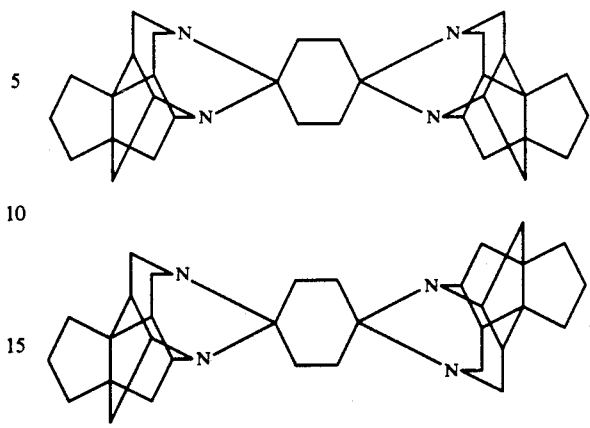

12. Derivatives according to claim 9, represented by

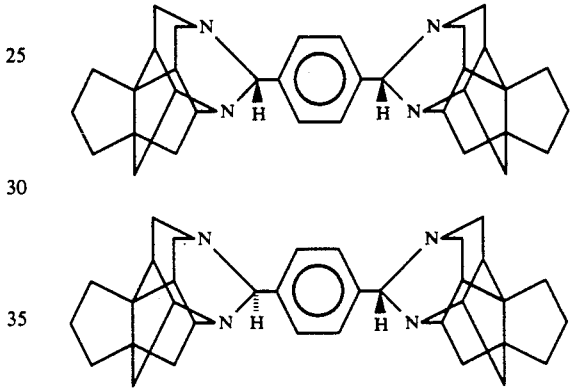

* * * * *

UNITED STATES PATENT AND TRADEMARK OFFICE
CERTIFICATE OF CORRECTION

PATENT NO. : 5,124,454

DATED : June 23, 1992

INVENTOR(S) : Drtina et al.

It is certified that error appears in the above-identified patent and that said Letters Patent is hereby corrected as shown below:

In Col. 2, line 39; Col. 2, line 56; Col. 3, line 36; Col. 7, line 58; Col. 8, line 8; Col. 8, line 11; Col. 8, line 37; Col. 9, line 45; and Col. 13, line 13, replace "animal" with --aminal--

Col. 7, line 32, Replace "H" with --$^1$H--

Col. 13, Formula III immediately above line 11 of text, Replace the "Y" with --$CH_2$--

Signed and Sealed this

Twelfth Day of October, 1993

Attest:

BRUCE LEHMAN

Attesting Officer     Commissioner of Patents and Trademarks